United States Patent
Wagner (12)

(10) Patent No.: US 6,840,771 B1
(45) Date of Patent: Jan. 11, 2005

(54) TOOTH WHITENING APPLIANCE

(76) Inventor: Eugene C. Wagner, 1626 Chastain Pkwy. East, Pacific Palisades, CA (US) 90272

(*) Notice: Subject to any disclaimer, the term of this patent is extended or adjusted under 35 U.S.C. 154(b) by 57 days.

(21) Appl. No.: 10/423,664

(22) Filed: Apr. 25, 2003

(51) Int. Cl.7 ............................................... A61C 15/00
(52) U.S. Cl. ....................................... 433/214; 433/216
(58) Field of Search ............................ 433/215, 6, 80, 433/216, 214; 604/77

(56) References Cited

U.S. PATENT DOCUMENTS

| | | |
|---|---|---|
| 3,527,219 A | 9/1970 | Greenberg |
| 3,567,823 A | 3/1971 | Yamaga |
| 3,624,909 A | 12/1971 | Greenberg |
| 4,173,219 A * | 11/1979 | Lentine ................ 604/77 |
| 4,776,792 A | 10/1988 | Wagner |
| 5,165,424 A | 11/1992 | Silverman |
| 5,302,374 A | 4/1994 | Wagner |
| 5,562,449 A | 10/1996 | Jacobs |
| 5,566,684 A | 10/1996 | Wagner |
| 5,575,654 A | 11/1996 | Fontenot |
| 5,611,687 A | 3/1997 | Wagner |
| 5,863,202 A | 1/1999 | Fontenot |
| 5,891,453 A | 4/1999 | Sagel |
| 6,096,328 A | 8/2000 | Sagel |
| 6,274,122 B1 | 8/2001 | McLaughlin |
| 6,364,665 B1 | 4/2002 | Trettenero |
| 6,379,147 B1 | 4/2002 | Georgakis |
| 6,506,053 B2 | 1/2003 | Wiesel |
| 6,514,484 B2 | 2/2003 | Rajaiah |
| 6,517,350 B2 | 2/2003 | Diasti |
| 2001/0044096 A1 * | 11/2001 | Lindquist .............. 433/215 |

* cited by examiner

Primary Examiner—Todd E. Manahan
(74) Attorney, Agent, or Firm—Seth Natter; Natter & Natter

(57) ABSTRACT

An appliance for the application of a tooth whitening preparation comprises an applicator configured as a partial dentition arch. The applicator includes an outer casing panel, to which is adhered a formative inner liner having a relatively low softening temperature. The applicator is user fitted by immersion in hot water to soften the liner which is then impressed against buccal tooth surfaces. A tooth whitening preparation is deposited upon the buccal impressions formed in a fitted liner or is directly applied to buccal tooth surfaces. Thereafter, the appliance is worn for prescribed treatment duration, precluding dilution of the tooth whitening preparation as well as assuring against gingival contact with such preparation.

20 Claims, 2 Drawing Sheets

TOOTH WHITENING APPLIANCE

BACKGROUND OF THE INVENTION

1. Field of the Invention

This invention relates generally to oral hygiene and more particularly to an appliance, which assures even and efficacious delivery of a tooth whitening preparation to buccal surfaces of target teeth for a prescribed treatment duration.

2. Antecedents of the Invention

Significant advances in the art of tooth whitening have evolved in recent years. Tooth whitening is no longer relegated to the costly and time consuming procedures rendered by the dental practitioner. Various approaches have evolved for practicing tooth whitening procedures without participation of the dental practitioner.

Among the early tooth whitening systems for do-it-yourself usage was a paste or gel containing a hydrogen peroxide or carbamide peroxide constituent. The gel or paste was applied to tooth surfaces by, for example, a toothbrush, a cotton swab, etc.

Unfortunately, such systems failed to provide readily noticeable results, due to a combination of factors including the limited time duration of application as well as the dilution of effective whitening or bleaching constituent within the oral cavity by saliva. Further, gingival surfaces were engaged by the whitening or bleaching constituent, leading to possible gingival initiation or other undesired effects.

Improved tooth whitening procedures included the admixture of conventional toothpaste together with a tooth whitening preparation, as described in U.S. Pat. No. 5,302,374 issued Apr. 12, 1994 and U.S. Pat. No. 5,597,554 issued Jan. 28, 1997 to applicant herein. The employment of such technique resulted in decreased tooth surface wear as well as an increase in the rate of efficacious release of the whitening or bleaching constituent of the tooth whitening preparation.

A further approach at providing an effective delivery system for a tooth whitening preparation on buccal enamel surfaces of target teeth included the system disclosed in U.S. Pat. No. 5,611,687 issued Mar. 18, 1997 to applicant herein. Such system comprised and applicator for carrying and applying a liquid preparation solely upon buccal surfaces of target teeth, i.e. teeth which are visible when talking, smiling, etc. The liquid preparation was drawn to an applicator tip by capillary action. To administer a coating of the tooth whitening preparation on selected tooth enamel surfaces, the tip was wiped over the surfaces to be treated.

Other attempts for improving the self administration of tooth whitening preparations included utilizing a fitted dental trough which surrounded buccal, occlusal and lingual tooth surfaces, as disclosed in U.S. Pat. No. 5,165,424 issued Nov. 24, 1992. The system disclosed therein did not attain widespread commercial success, perhaps due to the fact that the device was ungainly and impeded speech. It could not, therefore, be worn in any environment wherein social encounters might be anticipated. Further, the device did not assure the administration of tooth whitening preparation on only selected tooth surfaces and only to selected target teeth.

A further approach comprised the utilization of flexible strips preloaded with a tooth whitening preparation, as disclosed in U.S. Pat. No. 5,891,453 issued Apr. 6, 1999. The flexible strips disclosed therein were unable to attain a true impression of the user's buccal dentition; it could not intimately enter interdental crevices, for example. Further, the user was not able to control the concentration of tooth whitening preparation or limit the application to selected target teeth or tooth surfaces. A further disadvantage was that the tooth whitening preparation was often in contact with gingival surfaces, which often led to gingival irritation.

SUMMARY OF THE INVENTION

A tooth whitening appliance comprises an applicator having the configuration of a partial dentition arch. The applicator includes a thermoplastic outer casing which is generally "L" shaped in transverse cross section, having a ledge configured to extend at least partially between opposed occlusal surfaces. The inner face of the casing carries an impressionable formative liner of thermoplastic material having a softening temperature below that of the casing.

After heating the appliance in hot water to soften the liner, the liner is impressed against buccal surfaces of target teeth by applying pressure against the casing. An impression of buccal surfaces of target teeth to be whitened is thus formed in the liner.

The impressions, or selected impressions, thereafter receive a tooth whitening preparation. Alternatively or conjunctively, a tooth whitening preparation is applied to the buccal surfaces of target teeth. Thereafter, the appliance is reapplied against the buccal surfaces of the target teeth to provide intimate undiluted engagement between the tooth whitening preparation and the buccal surfaces to be whitened.

Separate appliances are fitted for the maxillary dentition and the mandibular dentition for simultaneous tooth whitening treatment of target teeth in both or the maxillary and mandibular dentitions may be treated individually. In an alternate embodiment, a single casing having upper and lower formative liners separated by a ledge may be employed for simultaneous fitting and for simultaneous treatment of target teeth of both dentitions.

From the foregoing compendium, it will be appreciated that it is an aspect of the present invention to provide a tooth whitening appliance of the general character described which is not subject to the disadvantages of the antecedents of the invention aforementioned.

It is a feature of the present invention to provide a tooth whitening appliance of the general character described having a simplified procedure for custom fitting.

A consideration of the present invention is to provide a tooth whitening appliance of the general character described which precludes undesirable gingival exposure to tooth whitening preparations.

A further aspect of the present invention is to provide a tooth whitening appliance of the general character described which assures against dilution of a tooth whitening preparation.

To provide a tooth whitening appliance of the general character described which does not impede speech is a further consideration of the present invention.

Another feature of the present invention is to provide a tooth whitening appliance of the general character described which is low in cost and suitable for manufacture by economical mass production fabrication.

To provide a tooth whitening appliance of the general character described which permits the user to vary the quantity of tooth whitening preparation applied to selected tooth surfaces is a further aspect of the present invention.

Another feature of the present invention is to provide a tooth whitening appliance of the general character described which is compatible with the administration of any of a number of available tooth whitening preparations.

A still further aspect of the present invention is to provide a tooth whitening appliance of the general character described which is both safe and efficacious.

Yet another feature of the present invention is to provide a tooth whitening appliance of the general character described which does not socially inhibit a user's movement from place to place during tooth whitening treatment.

Other aspects, features and considerations of the present invention in part will be obvious and in part will be pointed out hereinafter.

With these ends in view, the invention finds embodiment in the various combinations of elements, arrangements of parts and series of steps by which the said aspects, features and considerations aforementioned and certain other aspects, features and considerations are attained, all with reference to the following description and drawings and the scope of which will be more particularly pointed out and indicated in the appended claims.

BRIEF DESCRIPTION OF THE DRAWINGS

In the accompanying drawings in which are shown some of the various exemplary embodiments of the invention.

DESCRIPTION OF THE PREFERRED EMBODIMENTS

Figure 1:
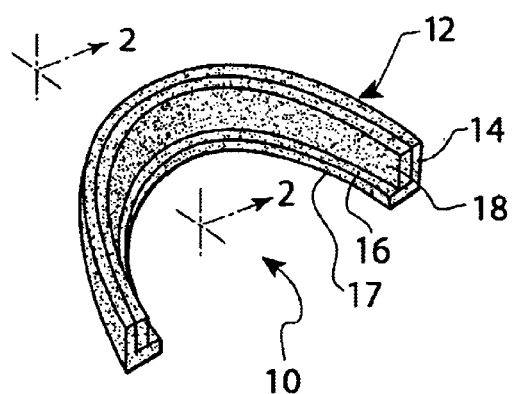
FIG. 1 is a perspective illustration of a tooth whitening appliance constructed in accordance with and embodying the invention prior to custom fitting and illustrating a curved outer shell and a formative inner liner.

Referring now in detail to the drawings, the reference numeral 10 denotes generally a tooth whitening appliance constructed in accordance with and embodying the invention. The appliance 10 is generally "C" rather than "U" shaped and does not register with a complete dentition. In accordance with the invention, the tooth whitening appliance 10 provides efficacious tooth whitening of only selected surfaces, i.e. the surfaces which are visible when smiling or speaking, for example. Accordingly, the tooth whitening appliance 10 is configured for the whitening of buccal enamel surfaces of only target teeth, as will be exemplified hereinafter.

Pursuant to the invention, the tooth whitening appliance 10 includes an outer casing 12 formed of a thermoplastic which, although yieldable, maintains its shape at oral cavity temperatures and is well suited for oral application. Examples of suitable thermoplastics for implementation as the outer casing 12 include polypropylene, polybutylene, polyethylene, polyvinyl chloride, polyurethane, ethylene vinyl acetate copolymer, or other similar materials suitable for usage in the oral cavity as disclosed in U.S. Pat. No. 5,566,684 issued to applicant herein as well as U.S. Pat. No. 3,624,909 and U.S. Pat. No. 5,863,202 all of which are incorporated herein by reference.

Figure 2:
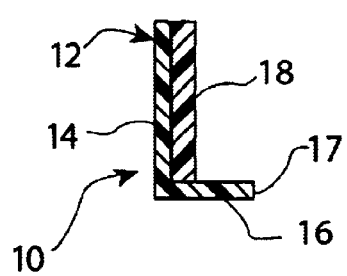
FIG. 2 is an enlarged scale sectional view through the appliance, the same taken substantially about the plane 2—2 of FIG. 1 and better illustrating a transverse ledge which projects inwardly from the casing.

As illustrated in FIG. 2, the casing 12 is generally "L" shaped in transverse cross section and includes an arcuate semi-cylindrical panel 14 and an integral perpendicular ledge 16 having a free distal edge 17.

Carried on the inner face of the arcuate panel 14 is a formative liner 18 which preferably comprises a thermoplastic resin having a lower softening temperature than that of the casing and which is employed to take an impression of the buccal surfaces of the target teeth. Suitable thermoplastics having Theological characteristics for implementation as the formative liner include thermoplastics which are deformable at temperatures below those which would cause discomfort or burning within the oral cavity during a fitting procedure, including those disclosed in U.S. Pat. No. 5,566,684 issued to applicant herein and U.S. Pat. No. 5,503,552.

The formative liner 18 may, but it not required to be adhered to the inner face of the panel 14. Adhesion can be obtained through known fabrication techniques, including molding the liner 18 over the outer casing 12 as disclosed in U.S. Pat. No. 5,566,684, as well as the use of adhesives or other bonding agents.

Transparent thermoplastics may be employed for both the casing 12 and the formative liner 18 so that the appliance will not attract attention when used.

Figure 3:
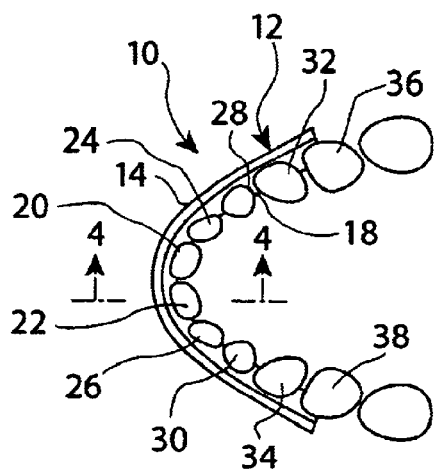
FIG. 3 is a bottom view of the appliance in engagement with selected target teeth of a maxillary dentition.

As heretofore mentioned, the tooth whitening appliance 10 is constructed to facilitate administration of a tooth whitening preparation only upon desired dentition surfaces, such surfaces being those which are normally exposed to view when one's mouth is opened or when one smiles. With reference to FIG. 3 comprising a bottom view of a maxillary dentition arch, it should be noted that the arch is generally symmetrically arrayed and includes at least a pair of central incisors 20, 22, a pair of lateral incisors 24, 26, a pair of cuspid 28, 30, a pair of first bicuspids 32, 34 and a pair of second bicuspids 36, 38.

Generally, the target teeth for tooth whitening comprise the central incisors 20, 22, the lateral incisors, 22, 24 the cuspid 26, 28 and the first bicuspids 32, 34. For some people, tooth whitening may also be desirable on the buccal surfaces of the second bicuspids. The appliance 10 is provided in predetermined sizes and shapes, however, it may be furnished in varying lengths such as to accommodate the second bicuspids or may be universally provided of an extended length, with the user trimming both ends such that the trimmed appliance will accommodate the target teeth. Additionally, the inner face of the liner 18 may include preformed tooth surface indentations for guidance in placement during the fitting procedure.

In accordance with the invention, if the liner is required to be softened by heating, the appliance is immersed in water at or near boiling temperature for a prescribed duration sufficient to heat the formative liner 18 to a softened state, wherein it is readily pliable and capable of taking an impression of tooth surfaces. The appliance is then removed from the hot water, allowed to cool slightly, such that it will not burn tissue or cause extensive discomfort when placed in the mouth, and thereafter impressed against buccal surfaces of the target teeth through the application of pressure against the panel 14 to assume a final position indicated in FIG. 3, wherein the formable liner 18 has conformed to the buccal surfaces of the target teeth and entered interdental intertistices. It should be noted that during the fitting procedure, the ledge 16 serves as a guide, engaging and sliding over or under occlusal surfaces.

Figure 4:
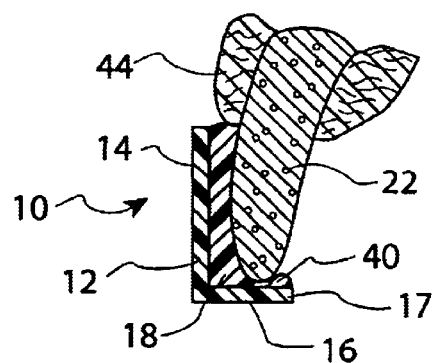
FIG. 4 is an enlarged scale sectional view, the same being taken substantially along the plane 4—4 of FIG. 3 and showing the formative liner contoured with the impression of the buccal surface of a user's central incisor.

With reference now to FIG. 4, it will be seen that a portion or portions of the formative liner 18 may extrude between the occlusal tooth surfaces and the ledge and form a bead 40 on the lingual face of a tooth. The bead 40 serves to retain or lock the tooth whitening appliance 10 in its fitted position so as not to impede speech or other functions when being worn during administration of the tooth whitening preparation.

Figure 5:
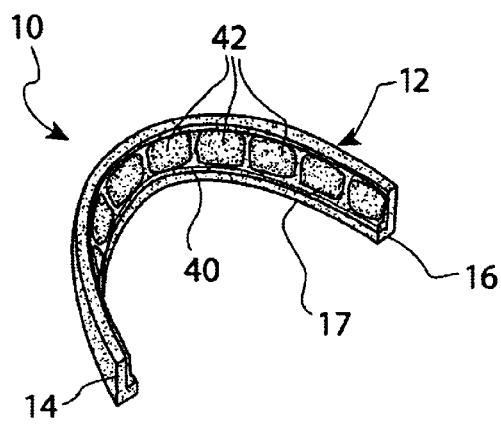
FIG. 5 is a perspective view of the tooth whitening appliance after having been fitted and illustrating impressed contours of buccal surfaces of the user's target teeth.
Figure 6:
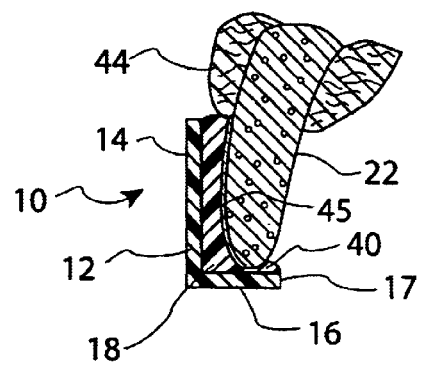
FIG. 6 is a sectional view, similar to FIG. 4, illustrating the tooth whitening appliance in use during the administration of a tooth whitening preparation.

After cooling to oral cavity temperature, the appliance 10 is removed from the oral cavity, however, the inner face of the liner 18 bears impressions 42 of the buccal tooth surfaces, as illustrated in FIG. 5.

Thereafter, a layer or coating 45 of any of a number of available tooth whitening preparations including pastes, liquids and gels or combinations thereof may be applied to some or all of the impressions 42 and the appliance is applied against the buccal tooth surfaces of the target teeth to administer the tooth whitening preparation.

Alternatively or conjunctively, a layer or coating 45 of tooth whitening preparation may be applied to the buccal enamel surfaces of the target teeth before the appliance is applied during administration.

The appliance is maintained in its applied position, assuring intimate contact between the layer 45 of the tooth whitening preparation and the buccal enamel surfaces of the target teeth for a prescribed treatment duration. The fitted appliance may be reused indefinitely to administer tooth whitening preparation in successive treatments.

It should be noted that employment of the tooth whitening appliance assures that tooth whitening preparation will not inadvertently contact and possibly irritate gingival surfaces 44 and also assures that the tooth whitening preparation itself will not be subject to dilution or diminution in effectiveness resulting from contact with saliva.

Figure 7:
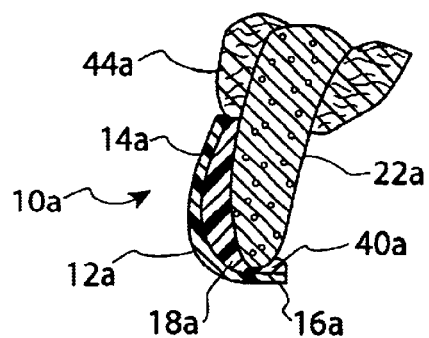
FIG. 7 is an enlarged scale sectional view, similar to the view of FIG. 4, through an alternate embodiment of the tooth whitening appliance, wherein the casing is curved.

In FIG. 7 there is illustrated the alternate embodiment of the invention wherein like numerals have been employed to designate like components of the previous embodiment, however, bearing the suffix "a". A tooth whitening appliance 10a includes an outer casing 12a formed of an arcuate panel 14a and a transverse ledge 16a. A formative liner 18a is adhered to the inner face of the panel 14a.

FIG. 7 depicts the fitting procedure wherein the heated formative liner 18a has been pressed against the buccal tooth surfaces of a central incisor 22a and conforms to such shape, with a bead 40a engaging a lingual surface of the incisor 22a.

The curved panel 14a serves to more precisely confine the areas wherein the heated formable liner 18a will flow during the fitting procedure and assures that a seal will be provided to preclude the tooth whitening preparation from contacting gingival surfaces 44a.

Figure 8:
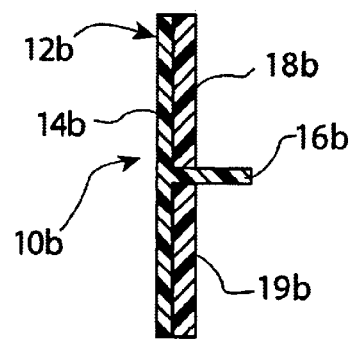
FIG. 8 is an enlarged scale sectional view, similar to the view of FIG. 2, through a further embodiment of the invention, wherein the tooth whitening appliance is configured for simultaneous fitting and subsequent usage in connection with the whitening of buccal tooth surfaces of target teeth in both the maxillary and mandibular dentitions.

In FIG. 8 there is illustrated a further embodiment of the invention wherein like numerals have been employed to designate like components of the prior embodiments, however, bearing the suffix "b".

A tooth whitening appliance 10b includes an outer casing 12b having a panel 14b which is essentially twice the height of the panel 14 of the prior embodiment and includes a central perpendicular ledge 16b having a free distal edge. Adhered to the inner face of the panel 14b above the ledge 16b is a formative liner 18b and adhered to the inner face of the panel 14b below the ledge 16b is a further formative line 19b.

It should be readily appreciated that the tooth whitening appliance 10b is fitted in a procedure substantially identically to that of the prior embodiments and is employed to simultaneously obtain the impressions of the buccal surfaces of target teeth in both the maxillary and mandibular dentitions and also provides simultaneous administration of tooth whitening preparation to the buccal surfaces of target teeth in both dentitions.

Thus it will be sent that there is provided a tooth whitening appliance which achieves the various aspects, features and considerations of the present invention and which is well adapted to meet the conditions of practical usage.

Since various possible embodiments might be made of the present invention and since various changes might be made in the exemplary embodiments set forth herein without departing from the spirit of the invention, is to be understood that all matter herein described or shown in the accompanying drawings is to be interpreted as illustrative and not in a limiting sense.

What is claimed is:

1. A tooth whitening appliance for the administration of a tooth whitening preparation, the appliance having a plan configuration for overlying buccal surfaces of selected target teeth of a dental arch, the appliance comprising a casing and a formative liner, the casing including a panel and a transverse ledge extending from the panel, the ledge having a free distal edge, the ledge being configured to engage occlusal surfaces of target teeth, the panel and the ledge defining a substantially "L" shaped transverse cross section throughout the casing, the formative liner having theological characteristics suitable for implementation as a dental impression material, the formative liner being carried by the panel, the formative liner receiving the impression of the buccal surfaces of the target teeth when the appliance is fitted, the formative liner being adapted to overlie a tooth whitening preparation positioned between the buccal surfaces and the impression of the buccal surfaces during administration of the tooth whitening preparation.

2. A tooth whitening appliance for the administration of a tooth whitening preparation as constructed in accordance with claim 1 wherein the formative liner is bonded to the panel.

3. A tooth whitening appliance for the administration of a tooth whitening preparation as constructed in accordance with claim 1 wherein the ledge is perpendicular to the panel.

4. A tooth whitening appliance for the administration of a tooth whitening preparation as constructed in accordance with claim 1 wherein the panel is curved in transverse cross section.

5. A tooth whitening appliance for the administration of a tooth whitening preparation as constructed in accordance with claim 1 wherein the panel and the liner are formed of clear thermoplastic.

6. A tooth whitening appliance for the administration of a tooth whitening preparation as constructed in accordance with claim 1 wherein the casing and the liner are formed and of transparent materials.

7. A tooth whitening appliance for the administration of a tooth whitening preparation as constructed in accordance with claim 1 wherein the casing and the liner are formed of thermoplastic resins.

8. A method of practicing the oral hygiene art of tooth whitening utilizing a tooth whitening preparation, the method comprising the steps of:
   a) providing a tooth whitening appliance having a casing with a substantially "L-shaped transverse cross section throughout and a formative thermoplastic liner carried by the casing, the liner having rheological characteristics suitable for implementation as a dental impression material,
   b) heating the appliance to a temperature above the softening point of the liner,
   c) obtaining in the liner an impression of buccal surfaces of selected target teeth by inserting the appliance in the oral cavity and applying lateral pressure against the casing to force the liner against the buccal surfaces of selected target teeth,
   d) removing the appliance after the liner has cooled, and
   e) administering the tooth whitening preparation to the buccal surfaces by covering the buccal surfaces with the liner and with a layer of tooth whitening preparation between the buccal surfaces and the impression formed in the liner.

9. A method of practicing the oral hygiene art of tooth whitening in accordance with claim 8 wherein the step of administering the tooth whitening preparation includes applying a layer of tooth whitening preparation to the impression of buccal surfaces formed in the liner and thereafter covering the buccal surfaces of the selected target teeth with the liner.

10. A method of practicing the oral hygiene art of tooth whitening in accordance with claim 9 wherein the step of administering includes applying a layer of tooth whitening preparation to the buccal surfaces of selected target teeth prior to covering the buccal surfaces.

11. A method of practicing the oral hygiene art of tooth whitening in accordance with claim 8 wherein the step of administering the tooth whitening preparation includes applying a layer of tooth whitening preparation to the buccal surfaces of selected target teeth and thereafter covering the buccal surfaces with the liner.

12. A method of practicing the oral hygiene art of tooth whitening in accordance with claim 8 wherein the casing includes a transverse ledge having a free end, the step of obtaining an impression being performed while the occlusal surfaces of the target teeth are in contact with the ledge.

13. A method of practicing the oral hygiene art of tooth whitening in accordance with claim 12 wherein the step of obtaining an impression includes extruding a bead of liner material in contact with lingual surfaces of selected teeth.

14. A method of practicing the oral hygiene art of tooth whitening in accordance with claim 8 further including the steps of:
   f) uncovering the buccal surfaces after a prescribed tooth whitening treatment duration has been concluded, and
   g) administering a subsequent treatment of tooth whitening preparation by repeating step e).

15. A method of practicing the oral hygiene art of tooth whitening in accordance with claim 8 wherein separate tooth whitening appliances are provided for the maxillary dentition and for the mandibular dentition and the remaining steps are practiced with respect to each dentition.

16. A method of practicing the oral hygiene art of tooth whitening utilizing a tooth whitening preparation, the method comprising the steps of:
   a) providing a tooth whitening appliance having a casing and a formative thermoplastic liner, the formative liner having rheological characteristics suitable for implementation as a dental impression material,
   b) heating the appliance to a temperature above the softening point of the formative liner,
   c) positioning the appliance in registration with selected target teeth by inserting the appliance into an oral cavity and moving the appliance laterally toward buccal surfaces of the selected target teeth without biting,
   d) obtaining in the liner an impression of the buccal surfaces by applying lateral pressure against the casing to force the liner against the buccal surfaces without biting,
   e) removing the appliance after the liner has cooled, and
   f) administering the tooth whitening preparation to the buccal surfaces by covering the buccal surfaces with the liner and with a layer of tooth whitening preparation between the buccal surfaces and the impression formed in the liner.

17. A method of practicing the oral hygiene art of tooth whitening in accordance with claim 16 further including the step of separating the liner from the casing prior to step f).

18. A tooth whitening appliance for the administration of a tooth whitening preparation, the appliance having a "C" shaped plan configuration for overlying buccal surfaces of selected target teeth of less than a complete dental arch, the selected target teeth consisting of central incisors, lateral incisors, cuspids and bicuspids, the appliance comprising a casing and a formative liner, the casing including a panel and a transverse ledge extending from the panel, the ledge having a free distal edge, the formative liner having rheological characteristics suitable for implementation as a dental impression material, the formative liner being carried by the panel, the formative liner receiving the impression of the buccal surfaces of the target teeth when the appliance is fitted, the formative liner being adapted to overlie a tooth whitening preparation positioned between the buccal surfaces and the impression of the buccal surfaces during administration of the tooth whitening preparation.

19. A tooth whitening appliance for the administration of a tooth whitening preparation as constructed in accordance with claim 18 wherein the selected target teeth consist of central incisors, lateral incisors, cuspids and first bicuspids.

20. A tooth whitening appliance for the administration of a tooth whitening preparation as constructed in accordance with claim 18 wherein the panel and the ledge define a substantially "L" shaped cross section throughout the casing.

* * * * *